(12) United States Patent
Harvey

(10) Patent No.: US 9,157,040 B2
(45) Date of Patent: Oct. 13, 2015

(54) RENEWABLE HIGH DENSITY TURBINE AND DIESEL FUELS

(71) Applicant: THE UNITED STATES OF AMERICA AS REPRESENTED BY THE SECRETARY OF THE NAVY, Washington, DC (US)

(72) Inventor: Benjamin G. Harvey, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 261 days.

(21) Appl. No.: 13/861,198

(22) Filed: Apr. 11, 2013

(65) Prior Publication Data

US 2015/0011809 A1    Jan. 8, 2015

Related U.S. Application Data

(60) Provisional application No. 61/624,757, filed on Apr. 16, 2012.

(51) Int. Cl.
| | | |
|---|---|---|
| C07C 1/24 | (2006.01) | |
| C07C 2/50 | (2006.01) | |
| C10L 1/04 | (2006.01) | |
| C12P 5/00 | (2006.01) | |
| C10G 45/44 | (2006.01) | |
| C10G 45/60 | (2006.01) | |
| C10G 3/00 | (2006.01) | |
| C12P 7/04 | (2006.01) | |

(52) U.S. Cl.
CPC ... *C10L 1/04* (2013.01); *C10G 3/42* (2013.01); *C10G 45/44* (2013.01); *C10G 45/60* (2013.01); *C12P 5/002* (2013.01); *C12P 7/04* (2013.01); *C10G 2300/1014* (2013.01); *C10G 2300/308* (2013.01)

(58) Field of Classification Search
USPC .......... 585/14, 317, 357, 361; 208/15, 16, 17
See application file for complete search history.

(56) References Cited

U.S. PATENT DOCUMENTS 4,286,109 A * 8/1981 Norton et al. .................. 585/14

* cited by examiner

*Primary Examiner* — Thuan D Dang
(74) *Attorney, Agent, or Firm* — Charlene A. Haley

(57) ABSTRACT

A method for synthesizing cyclic hydrocarbons with linear hydrocarbon side chains from a renewable source, or biomass by naturally occurring or bioengineered fungal strains, or hydrodistillation of plants.

17 Claims, 2 Drawing Sheets

US 9,157,040 B2

RENEWABLE HIGH DENSITY TURBINE AND DIESEL FUELS

CROSS-REFERENCE TO RELATED APPLICATIONS

This is a non-provisional patent application, claiming the benefit of, parent application Ser. No. 61/624,757 filed on Apr. 16, 2012, whereby the entire disclosure of which is incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to a process for the synthesis of a high density fuel from renewable sources including waste biomass.

Figure 1:
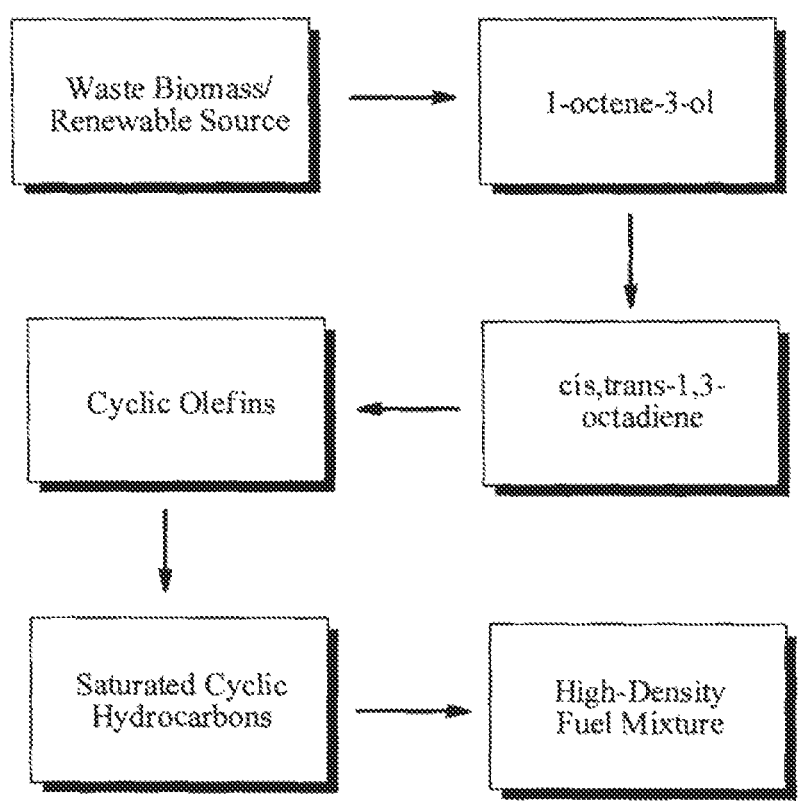
FIG. 1 is a diagram showing the process for synthesizing of high density fuels from renewable sources including waste biomass, according to embodiments of the invention.
Figure 2:
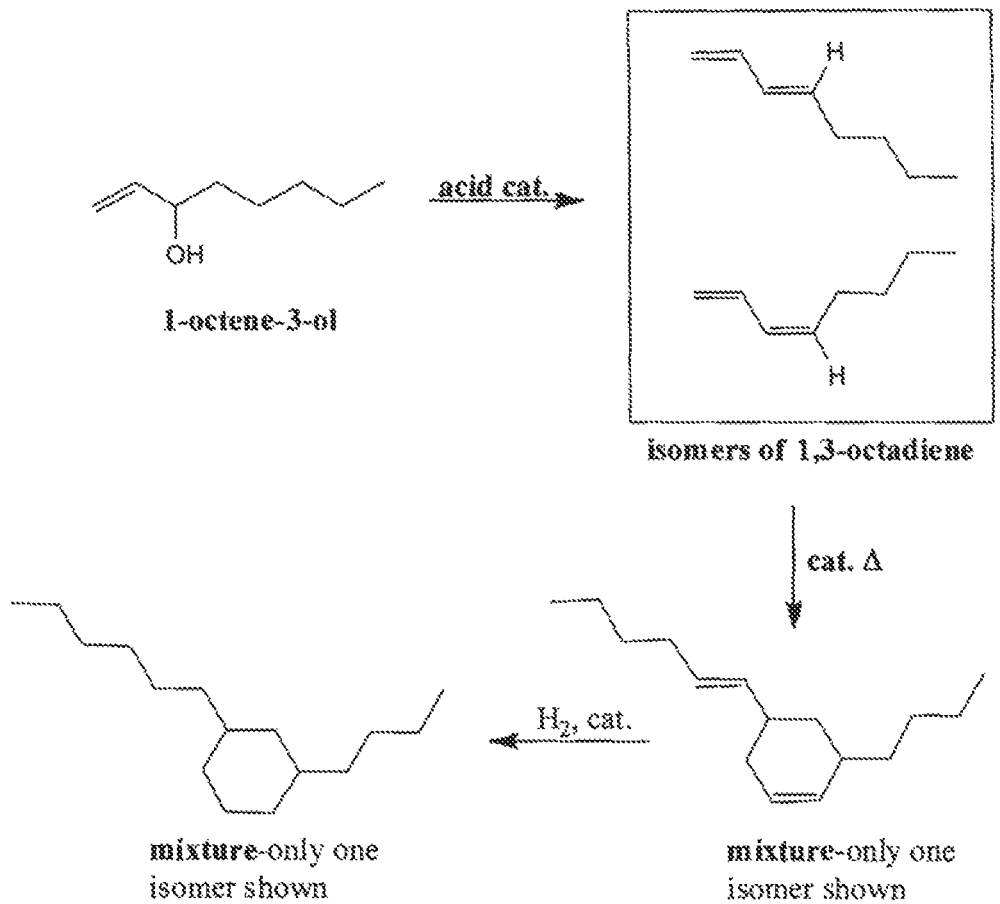
FIG. 2 is a chemical schematic showing the process for synthesizing of high density fuels from renewable sources including waste biomass, according to embodiments of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF THE EMBODIMENTS OF THE INVENTION

Embodiments of the invention generally relate to a process for the synthesis of a high density fuel from renewable sources including waste biomass.

High density renewable fuels have applications in a number of vehicle and weapon platforms. The use of fuels with high densities and net heats of combustion allows for improved tactical performance. In addition, use of renewable fuels decreases consumption of petroleum and is aligned with current and future Navy goals related to sustainability and greenhouse gas reduction.

Although research into renewable fuels has progressed at a rapid pace, particularly in the last decade, most renewable fuels synthesized for use as turbine or diesel fuels have modest densities that preclude them from being considered "full-performance" fuels. Petroleum derived filets contain a number of functional groups including aromatic and cyclic moieties that improve the density and the volumetric net heat of combustion of the fuel. As an additional limitation, diesel engines require hydrocarbon fuels with high centric numbers (a property derived from linear hydrocarbon chains) thus limiting the density achievable for renewable diesel fuels.

This invention describes a process to efficiently synthesize a cyclic hydrocarbon with linear hydrocarbon side chains from a renewable source. The resulting fuel mixture then has both a higher density than either straight chain or branched hydrocarbons and a high enough cetane number to be used in a diesel engine. These fuel mixtures have applications as both turbine and diesel fuels and have the potential to improve the tactical performance of aircraft, weapon systems, UAV's, and diesel powered vehicles, while greatly reducing the net greenhouse gas emissions and environmental impact of these platforms. Also of importance, these fuels can be derived from sustainable sources helping to stabilize fuel prices and reduce the reliance of the Navy on petroleum derived products.

Synthesizing cyclic hydrocarbons with linear hydrocarbon side chains from a renewable source, or biomass by naturally occurring or bioengineered fungal strains, or hydrodistillation of plants.

1-octene-3-ol is isolated from a renewable source or is produced by bioengineered organisms. 1-octene-3-ol is then dehydrated by a catalyst to produce a mixture of cis and trans 1,3-octadiene as well as isomerized octadienes (catalysts include inorganic acids, Lewis acids, solid acid catalysts). The mixture of octadienes is cyclodimerized with the aid of a catalyst, modest pressure, and heat. The resulting cyclic olefins are hydrogenated to produce a saturated mixture. The mixture is purified by distillation to yield a high density fuel.

In another embodiment, 1-octene-3-ol can be isolated from a number of renewable sources. Linoleic acid can be enzymatically broken down to produce 1-octene-3-ol. Alternatively, hydrodistillation of plants (e.g. *Melittis melissophyllum* subsp. *Melissophyllum*) or isolation of 1-octene-3-ol from the degradation of biomass by naturally occurring or bioengineered fungal strains can yield significant quantities of the alcohol. The alcohol is dehydrated with an acid catalyst to yield a mixture of cis and trans-1,3-octadiene. Suitable catalysts include inorganic acids including phosphoric, sulfuric, and hydrochloric acids. Solid acid catalysts including acid clays, various inorganic oxides, zeolites, aluminosilicates and cation exchange resins can also be used for the dehydration reaction. Homogenous or heterogeneous Lewis acid catalysts are also suitable for the dehydration reaction. A pure mixture of octadienes can be isolated by fractional distillation. The octadiene mixture is then mixed with either a homogenous or heterogeneous catalyst and heated in a dosed system under moderate pressure to affect a Diels-Alder cycloaddition. The resulting cyclic olefins are catalytically hydrogenated with the aid of a catalyst (Ni, Pd, Pt, Cu) to yield a saturated hydrocarbon product. The saturated mixture is distilled to yield the final high density fuels.

Embodiments of the invention generally relate to methods of synthesizing fuels including, isolating 1-octene-3-ol from waste biomass or a renewable source by hydrodistillation of plant material, enzymatic cleavage of fatty acids, or direct biosynthesis with fungi or bacteria, dehydrating 1-octene-3-ol with at least one acid catalyst to produce a mixture of isomers of 1,3-octadiene and internal octadienes, cyclodimerizing the mixture of isomers of 1,3-octadiene and internal octadienes under modest pressure having a range from about 1 atm to about 200 atm and beating with a range from about −20° C. to about 350° C. with at least one homogeneous or heterogenous Lewis acid catalyst to effect a Diels-Alder cycloaddition to produce a mixture of unsaturated cyclic olefins, catalytically hydrogenating the unsaturated cyclo-olefins with hydrogen to produce a mixture of saturated cyclic hydrocarbons, and purifying the saturated cyclic hydrocarbons by distillation to produce fuel mixtures with densities greater than 0.8 g/mL.

Another aspect of the invention generally relates to methods of synthesizing fuels including, isolating 1-octene-3-ol from waste biomass or a renewable source by hydrodistillation of plant material, enzymatic cleavage of fatty acids, or direct biosynthesis with fungi or bacteria dehydrating the 1-octene-3-ol with at least one acid catalyst to produce a mixture of isomers of 1,3-octadiene and internal octadienes, cyclodimerizing the mixture of isomers of 1,3-octadiene and internal octadienes with other renewable or petroleum derived conjugated dienes having between 4 and 20 carbon atoms, or any dienophile under modest pressure a range from about 1 atm to about 200 atm and heating with a range from about −20° C. to about 350° C. with at least one homogeneous or heterogenous catalyst to effect a Diels-Alder cycloaddition to produce a mixture of unsaturated cyclic olefins, catalytically hydrogenating the unsaturated cyclo-olefins with hydrogen to produce a mixture of saturated cyclic hydrocarbons, and purifying the saturated cyclic hydrocarbons by distillation to product fuel mixtures with densities exceeding 0.8 g/mL.

Embodiments further include isolating by degradation of said waste biomass having naturally occurring or bioengineered fungal strains. In other embodiments, the renewable source including at least one linoleic acid, other fatty acids, triglycerides, or mixtures thereof. Embodiments further include obtaining alcohol by hydrodistillation of a renewable source including plants being *Melittis melissophyllum*. In embodiments, the acid catalyst includes at least one inorganic acid selected from the group consisting of phosphoric acid, sulfuric acid, and hydrochloric acid, other mineral acids, and supported mineral acids. In other embodiments, the acid catalyst includes at least one solid acid catalyst selected from the group consisting of acid clays, inorganic oxides, zeolites, aluminosilicates, and cation exchange resins. Yet in other embodiments, the Lewis acid catalyst includes either homogenous or heterogeneous with an active component that includes a Group 3 metal, transition metal, or lanthanide metal. Still yet in other embodiments, the catalyst utilized in the catalytic hydrogenation includes at least one Pt, Pd, or Cu. In embodiments, the other renewable or petroleum derived conjugated dienes includes at least one butadiene, 2,3-dimethylbutadiene, isoprene, and any alkene. Another aspect of the invention includes fuel mixtures (including high density fuels) produced by the methods herein.

PROPHETIC EXAMPLES

Any of the prophetic examples are for illustration purposes only and not to be used to limit any of the embodiments.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A method of synthesizing fuels, comprising:
   isolating 1-octene-3-ol from waste biomass or a renewable source by hydrodistillation of plant material, enzymatic cleavage of fatty acids, or direct biosynthesis with fungi or bacteria;
   dehydrating said 1-octene-3-ol with at least one acid catalyst to produce a mixture of isomers of 1,3-octadiene and internal octadienes;
   cyclodimerizing said mixture of isomers of 1,3-octadiene and internal octadienes under modest pressure having a range from about 1 atm to about 200 atm and heating with a range from about −20° C. to about 350° C. with at least one homogeneous or heterogenous Lewis acid catalyst to effect a Diels-Alder cycloaddition to produce a mixture of unsaturated cyclic olefins;
   catalytically hydrogenating said unsaturated cyclo-olefins with hydrogen to produce a mixture of saturated cyclic hydrocarbons; and
   purifying said saturated cyclic hydrocarbons by distillation to produce fuel mixtures with densities greater than 0.8 g/mL.

2. The method according to claim 1, further comprising isolating by degradation of said waste biomass includes naturally occurring or bioengineered fungal strains.

3. The method according to claim 1, wherein said renewable source comprises at least one linoleic acid, other fatty acids, triglycerides, or mixtures thereof.

4. The method according to claim 1, further comprising obtaining alcohol by hydrodistillation of a renewable source including plants being *Melittis melissophyllum*.

5. The method according to claim 1, wherein said acid catalyst comprises at least one inorganic acid selected from the group consisting of phosphoric acid, sulfuric acid, and hydrochloric acid, other mineral acids, and supported mineral acids.

6. The method according to claim 1, wherein said acid catalyst comprises at least one solid acid catalyst selected from the group consisting of acid clays, inorganic oxides, zeolites, aluminosilicates, and cation exchange resins.

7. The method according to claim 1, wherein said Lewis acid catalyst comprises either homogenous or heterogeneous with an active component that includes a Group 3 metal, transition metal, or lanthanide metal.

8. The method according to claim 1, wherein said catalyst utilized in the catalytic hydrogenation comprises at least one Ni, Pt, Pd, or Cu.

9. A method of synthesizing fuels, comprising:
   isolating 1-octene-3-ol from waste biomass or a renewable source by hydrodistillation of plant material, enzymatic cleavage of fatty acids, or direct biosynthesis with fungi or bacteria;
   dehydrating said 1-octene-3-ol with at least one acid catalyst to produce a mixture of isomers of 1,3-octadiene and internal octadienes;
   cyclodimerizing said mixture of isomers of 1,3-octadiene and internal octadienes with other renewable or petroleum derived conjugated dienes having between 4 and 20 carbon atoms, or any dienophile under modest pressure a range from about 1 atm to about 200 atm and heating with a range from about −20° C. to about 350° C. with at least one homogeneous or heterogenous catalyst to effect a Diels-Alder cycloaddition to produce a mixture of unsaturated cyclic olefins;

catalytically hydrogenating said unsaturated cyclo-olefins with hydrogen to produce a mixture of saturated cyclic hydrocarbons; and purifying said saturated cyclic hydrocarbons by distillation to produce fuel mixtures with densities exceeding 0.8 g/mL.

10. The method according to claim 9, wherein said other renewable or petroleum derived conjugated dienes comprises at least one butadiene, 2,3-dimethylbutadiene, isoprene, and any alkene.

11. The method according to claim 9, further comprising isolating by degradation of said waste biomass includes naturally occurring or bioengineered fungal strains.

12. The method according to claim 9, wherein said renewable source comprises at least one linoleic acid, other fatty acids, triglycerides, or mixtures thereof.

13. The method according to claim 9, further comprising obtaining alcohol by hydrodistillation of a renewable source including plants being *Melittis melissophyllum*.

14. The method according to claim 9, wherein said acid catalyst comprises at least one inorganic acid selected from the group consisting of phosphoric acid, sulfuric acid, and hydrochloric acid, other mineral acids, and supported mineral acids.

15. The method according to claim 9, wherein said acid catalyst comprises at least one solid acid catalyst selected from the group consisting of acid clays, inorganic oxides, zeolites, aluminosilicates, and cation exchange resins.

16. The method according to claim 9, wherein said Lewis acid catalyst comprises either homogenous or heterogeneous with an active component that includes a Group 3 metal, transition metal, or lanthanide metal.

17. The method according to claim 9, wherein said catalyst utilized in the catalytic hydrogenation comprises at least one Ni, Pt, Pd, or Cu.

* * * * *